United States Patent [19]
Lau et al.

[11] Patent Number: 5,567,432
[45] Date of Patent: Oct. 22, 1996

[54] MASKING OF LIPOSOMES FROM RES RECOGNITION

[76] Inventors: John R. Lau, 585 King Beach Dr., Howard, Ohio 43028; W. Blair Geho, 533 Beechwood St., Wooster, Ohio 44691

[21] Appl. No.: 437,309

[22] Filed: May 9, 1995

Related U.S. Application Data

[63] Continuation of Ser. No. 8,779, Jan. 15, 1993, abandoned, which is a continuation-in-part of Ser. No. 739,485, Aug. 2, 1991, abandoned.

[51] Int. Cl.$^6$ .................................................. A61K 9/127
[52] U.S. Cl. ...................... 424/450; 428/402.2; 436/829
[58] Field of Search ...................... 424/450; 428/402.2; 436/829

[56] References Cited

U.S. PATENT DOCUMENTS

| | | | |
|---|---|---|---|
| 3,499,962 | 3/1970 | Wurzburg et al. | 424/35 |
| 3,960,757 | 6/1976 | Morishita et al. | 252/316 |
| 3,993,747 | 11/1976 | Gaffar et al. | 424/88 |
| 4,010,251 | 3/1977 | Green | 424/1.5 |
| 4,013,507 | 3/1977 | Rembaum | 195/1.8 |
| 4,116,776 | 9/1978 | Dalbow et al. | 195/103.7 |
| 4,187,194 | 2/1980 | Wellman et al. | 252/316 |
| 4,193,983 | 3/1980 | Ullman et al. | 424/12 |
| 4,224,179 | 9/1980 | Schneider | 252/316 |
| 4,225,487 | 9/1980 | Cuatrecasas et al. | 260/121 |
| 4,861,597 | 8/1989 | Kida et al. | 424/859 |
| 5,169,635 | 12/1992 | Ono et al. | 436/829 |

*Primary Examiner*—Gollamudi S. Kishore
*Attorney, Agent, or Firm*—Frijouf, Rust & Pyle

[57] ABSTRACT

A biochemical membrane encapsulated by a synthetically-derived neuraminic acid residue, to mask the surface of the membrane from recognition and removal by the scavenging RES cells of the body.

7 Claims, 9 Drawing Sheets

5-amino-3,5-dideoxy-D-glycero-D-galacto-2-
methoxy-nonulopyranose-1-onic acid

FIG. 5

2-iminothiolane
(Traut's Reagent)

β-methoxy neuraminic
acid 2-iminothiolane
—methoxyneuraminic
acid conjugate

MASKING OF LIPOSOMES FROM RES RECOGNITION

CROSS-REFERENCE TO RELATED APPLICATIONS

This application is a continuation of prior application Ser. No. 08/008,779 filed Jan. 15, 1993, now abandoned which in turn is a continuation-in-part of Ser. No. 07/739,485, filed Aug. 2, 1991, now abandoned.

DEFINITIONS

1. Sialic Acid

An N-acetyl derivative of neuraminic acid.

2. Neuraminic Acid

A synthetically-derived sialic acid. The Chemical Abstracts Index names for this molecule are: D-glycero-D-galacto-2-Nonulopyranosidonic acid, methyl 5-amino-3, 5-dideoxy(9C1); or D-glycero-D-galacto-Nonulopyranosidonic acid, methyl 5- amino-3, 5-dideoxy-(8C1). Another name for this molecule is Methoxyneuraminic Acid, or Beta-Methoxy Neuraminic Acid.

3. Particulate Matter

A RES recognizable antibody, protein antibody-drug conjugate, foreign substance, emulsion, albumin microsphere, dispersion, colloidal suspension, or any entity that has potential to be recognized or scavenged by the RES and that is greater than 10Å but less than 10μ.

BACKGROUND OF THE INVENTION

Liposomes, also known as vesicles have been designed to encapsulate a cargo of pharmacological agents useful for in vivo purposes such as the diagnosis and treatment of various diseases and conditions. In addition, particulate matter in the form of therapeutic emulsions used as drug carriers, for example, has been shown to enhance therapeutic indices. These cargo-carrying liposomes and particulate matter have, experimentally, shown potential for being site-specific carrier systems for a variety of such agents. Agents so delivered to designated sites in vivo demonstrate significantly enhanced therapeutic indices. Concurrently, a decrease in unwanted side effects and wasted portions of dosages are achieved. Agents not so couried spread to nonspecific and often undesirable areas of the body, and possibly cause side effects.

The advantages of the prior art in vive carrier system have been offset, however, by the deleterious effects of the body's reticuloendothelial system (the "RES"), mainly the liver and spleen. The RES is the body's defense system, acting to screen the body's circulation. The RES will gradually scavenge from the circulation all material it considers foreign. Liposomes and particulate matter have certain physical characteristics which render them susceptible to removal by the RES. Once recognized, liposomes and particulate matter, whether given or not given a site-specific molecule for site-specific delivery, are quickly phagocytosed by the RES along with their cargo. These prior revolutionary carrier systems have, until the present invention, and the preceding invention of U.S. Pat. No. 4,501,728, remained hampered by the RES.

In said earlier invention, U.S. Pat. No. 4,501,728, the sialic acid mechanism for RES avoidance is a system consisting essentially of a biochemical membrane having sialic acid residues that mask the surface membrane from recognition by the RES cells.

Despite the successful application of sialic acid residues to the liposome carrier system and particulate matter, liposomes so disguised from the RES were nevertheless eventually subject to enzymatic action of endogenous neuraminidase in the blood. Specifically, it was found that neuraminidase eventually cleaves the chemical bond between sialic acid and its attached sugar (galactose), thereby allowing the galactose (sugar) on the surface of the liposome to be recognized by the RES's Ashwell receptor of the liver.

Enzymatic removal of the sialic acid is time-dependent. Liposomes or particulate matter intended to circulate for longer periods of time in the vascular system or until localized to a binding-site, are removed by the RES once the sialic acid mask is compromised or lost.

SUMMARY OF THE PREFERRED EMBODIMENT OF THE INVENTION

This invention is embodied by the product of a procedure of applying to the external surface of a liposome carrier or particulate matter carrier a substituent molecule which masks the carrier from the RES and is selected from the class consisting of those chemicals which are classed biologically as synthetically derived molecules that significantly prevent phagocytosis by the body's RES and which cannot be degenerated and separated from the liposome or particulate matter by the action of circulating endogenous enzymes.

The carrier and its protective synthetically derived molecules, when constructed according to this invention, will allow the carrier to circulate in the blood system of the warm blooded host for an extended period of time without recognition by the RES. Thus, the carrier may be loaded with a burden such as insulin, and will feed the cargo of insulin into the blood stream gradually as it degenerates.

In applications of this invention, a target molecule may be employed, which molecule binds to or is bound by a specific site in the body and which is incorporated as part of the liposome carrier or particulate matter.

This invention is not concerned with the carrier or its contents, but only with the concept of masking the conjugate by means of a synthetically derived molecule that significantly prevents phagocytosis by the body's RES and which cannot be degenerated by the action of circulating endogenous enzymes.

Accordingly, the use of synthetically derived analogs of neuraminic acid will hold the masking action against the action of endogenous enzymes and therefore maintain the masking action.

The tandem effect of these substituent molecules achieves a biological result enhanced beyond expectation, as manifested by the improved delivery of the liposomal or particulate matter cargo. This degree of result was unanticipated from experience when these two substituent molecules were used one without the other.

It is a specific object of this invention to create, first, a composition of matter for in vivo administration of therapeutic or diagnostic agents, comprising a lipid membrane structure in the form of a liposome, also known as a vesicle, a second component which is a synthetically-derived molecule that prevents recognition of the liposome by the RES and which cannot be cleaved from the lipsome by the action of endogenous enzymes, and a third component which is a molecule that binds the liposome to a specific site or entity in the body and which can be present for site-specific delivery or absent for non-specific delivery of the therapeutic or diagnostic agents in vivo.

It is also an object of this invention to create a composition of matter for in vivo administration of therapeutic or diagnostic agents, comprising particulate matter which is >10Å but <10μ in diameter, a second component which is a synthetically-derived molecule that prevents recognition of the particulate matter by the RES and which cannot be cleaved from the particulate matter by the action of endogenous enzyme and a third component which is a molecule that binds the particulate matter to a specific site or entity in the body and which can be present for site-specific delivery or absent for non-specific delivery of the therapeutic or diagnostic agent in vivo.

This invention is the discovery that superior site-specific delivery of the liposome's or particulate matter's cargo is obtained by the combined effect of using synthetically-derived RES-avoidance molecules that cannot be cleaved by circulating endogenous enzymes, with site-specific binding molecules that find or are found by a receptor at a desired site in the body.

This invention is also the discovery that superior systemic circulation of liposomes or particulate matter without site-specific delivery, can be achieved using the aforementioned synthetic masking molecules without the site-binding molecule component.

DETAILED DESCRIPTION OF THE PREFERRED EMBODIMENT

This invention embodies a liposomal delivery system consisting essentially of a phospholipid membrane known commonly as vesicles, or liposomes (vesicles and liposomes, as used herein, mean the same thing), with two types of substituent molecules incorporated in the membrane. This invention also embodies a particulate matter delivery system using such two types of substitutent molecules.

One such type of molecule is classed biologically as a synthetic molecule which masks the liposome or particulate matter from the body's RES and which cannot be cleaved from the liposome or particulate matter by circulating endogenous enzymes. The other type of molecule is one which binds to a specific site in the body. The combination allows delivery of a greatly enhanced index of therapeutic or diagnostic cargo to such specific body site.

In the alternative, for superior circulatory lifetime of liposomes without site-specific delivery, the aforementioned site-specific binding molecule can be omitted. This superior circulatory lifetime would also pertain to particulate matter. B-methoxyneuraminic acid, used herein as a synthetic liposome or particulate matter masking molecule, is used in this description as an example and is preferred because its use is consistent with data shown herein.

The first example set forth hereinafter, is a liposome with a permeable membrane, which is designed and synthesized to circulate in the blood for an extended period of time as a non-binding time-release drug delivery system. Particulate matter can also be made to circulate in a similar fashion.

The second example set forth hereinafter, is a liposome which, in addition to being masked by the incorporation of neuraminic acid or its biologically-active derivatives onto the liposome membrane, is also invested with a site-binding molecule. Likewise this mask can be achieved for particulate matter as well. The inclusion of a site-binding molecule along with the neuraminic acid masking agent, creates a liposome or particulate matter which delivers its cargo to an appropriate specific site of action such as a tumor, with significantly less danger of being removed prematurely from the circulation by the RES.

Figure 1:
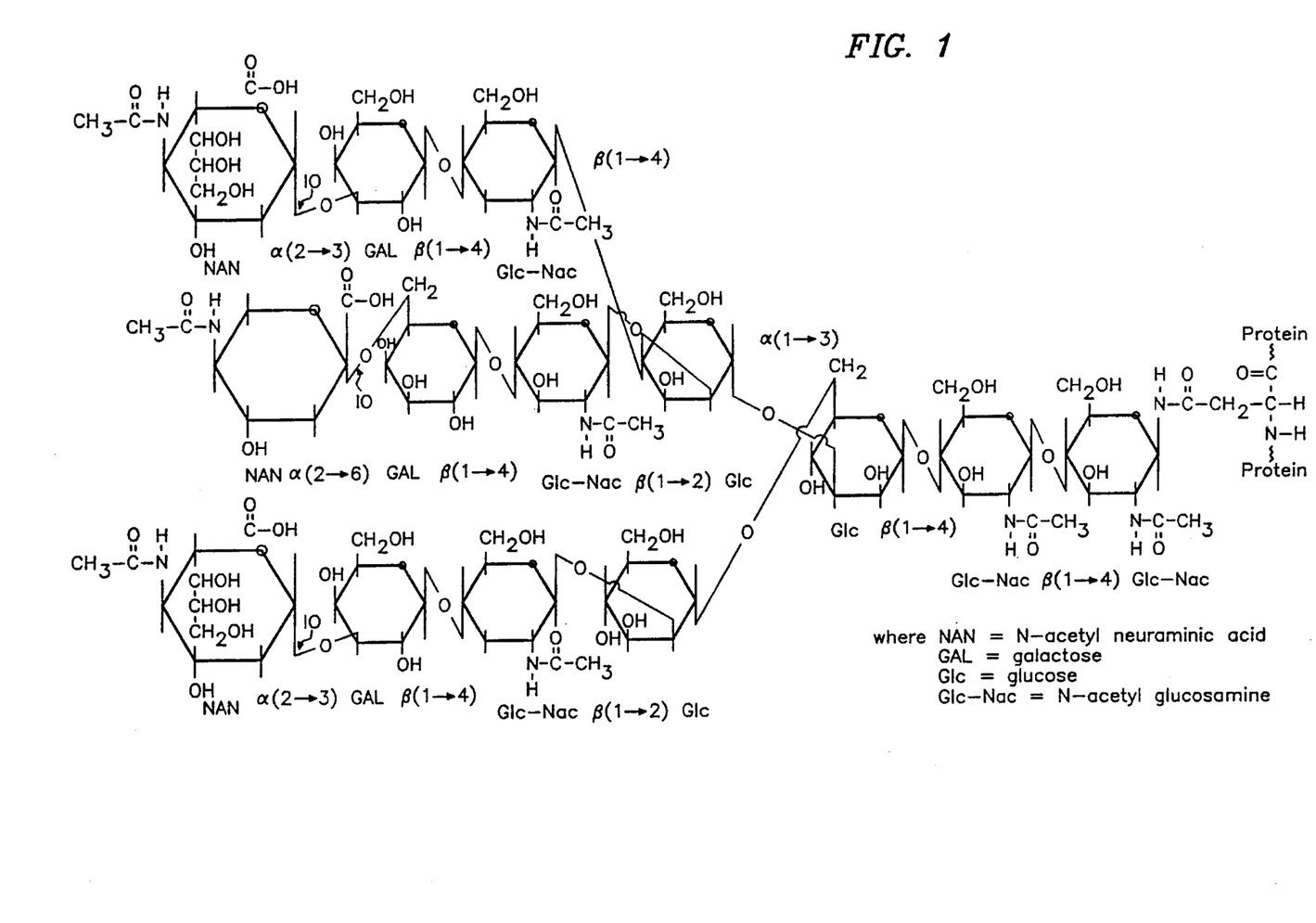
FIG. 1 is a representative of a branched glycoprotein that has sialic acid as the terminal units of the glycan chains.

It has been found, according to this invention, that the combination of masking plus a specific site-binding molecule, such as a monoclonal antibody for binding to tumor cells, produces a significant step beyond the expected benefits.

our U.S. Pat. No. 4,501,728 teaches and claims a means to use naturally-occurring sialic acid to avoid RES recognition. The structural formula for a glycoprotein with terminal sialic acid units is depicted in FIG. 1. A glycosidic bond connects the sialic acid to the penultimate sugar, usually a galactose as indicated by reference character "a".

Figure 1A:
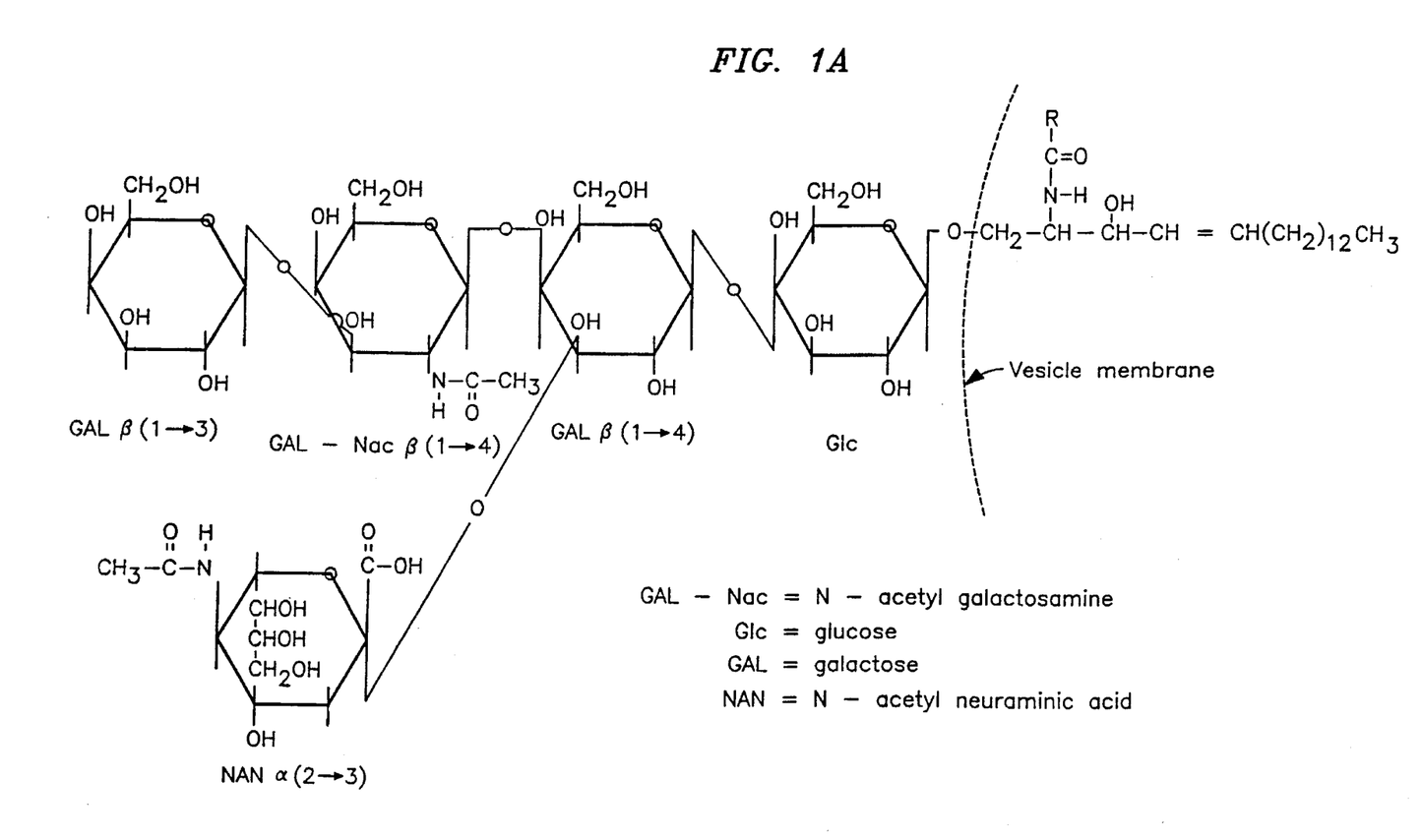
FIG. 1a represents a monosialoganglioside designated as $GM_1$. It is an example of a naturally occurring ganglioside wherein its sialic acid moiety is linked to an internal sugar.

Use of naturally-occurring sialic acid residues to mask liposomes or particulate matter from the RES enables liposomes or particulate matter to carry therapeutic or diagnostic agents in vivo for only limited periods of time. Liposomes and particulate matter masked with naturally-occurring sialic acid residues are subject to the action of circulating endogenous enzymes such as neuraminidase, which cleaves the glycosidic bond of the sialic acid, exposing its penultimate sugar to RES recognition, thereby facilitating their removal from the circulating system. The enzymatic cleavage of this glycosidic bond is by hydrolysis, and occurs at the bond indicated by reference character "a" of FIG. 1. The enzymatic cleavage of sialic acid may also occur on a sugar residue that is not penultimate but which is in the interior of the polymeric sugar chain. This glycosidic bond is shown in FIG. 1a and is indicated by reference character "c".

Despite the fact that RES masking is effectively achieved within certain restrictions or limitations using naturally-occurring sialic acid residues, it was discovered the that vastly improved masking-time can be achieved by using a synthetic sialic acid, such as Beta-methoxyneuramic acid, which cannot be cleaved and thus exposed to the RES by circulating endogenous enzymes. Therefore, the preferred best mode embodiment uses Beta-methoxyneuraminic acid, the systematic name of which is given above in the Definition section. See FIG. 2. Note that the sugar of this molecule has a free primary amino group (—$NH_2$—) attached to carbon #5 of the nonulopyranose ring structure, along with a non-reactive B-methoxy group (—$OCH_3$—) attached to carbon #2 of the ring.

The best mode product of this invention was found to be one in which the following was observed:

1) The bond of this invention is not susceptible to hydrolysis by the enzyme neuraminidase in the plasma of a warm blooded host;
2) The bond is stable both in vivo and in vitro for an indefinite period of time;
3) The bond can be of a secondary amine type;
4) The bond can be of a thioether type;
5) The bond is not readily hydrolyzable by other circulating endogenous enzymes in the plasma.
6) The bond can be an amide linkage involving a secondary amine and a carbonyl carbon.
7) The bond can be of a disulfide type.

Figure 3:
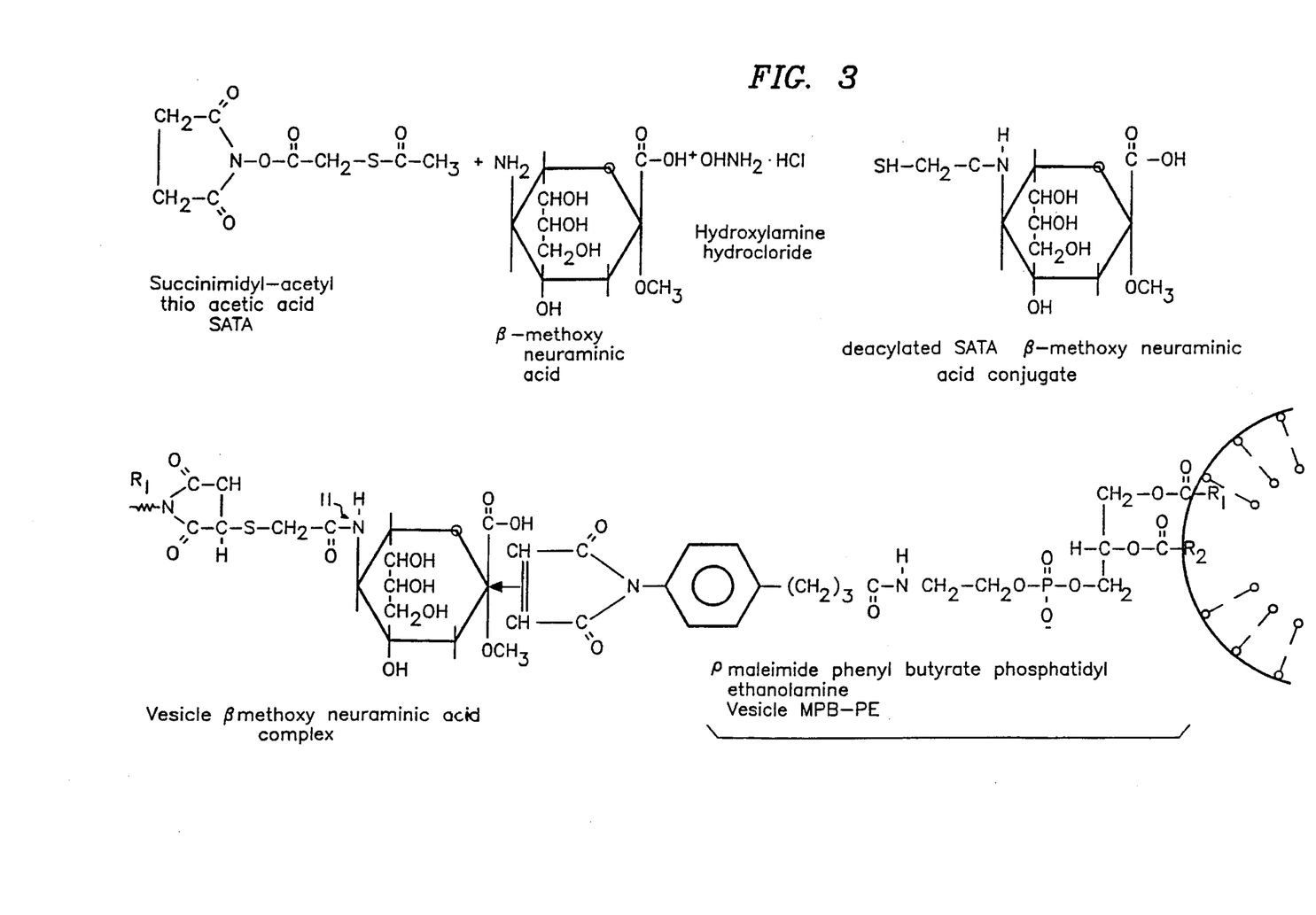
FIG. 3 illustrates the first example of a synthetic pathway by which a non- hydrolyzable secondary amide bond can be created by using an amide linkage to connect the B-methoxyneuraminic acid conjugate to an appropriate bridging molecule. The B-methoxy neuraminic acid complex can be incorporated into a liposome membrane as shown in FIG. 3 or mixed into the hydrophobic region of the appropriate particulate matter.
Figure 4:
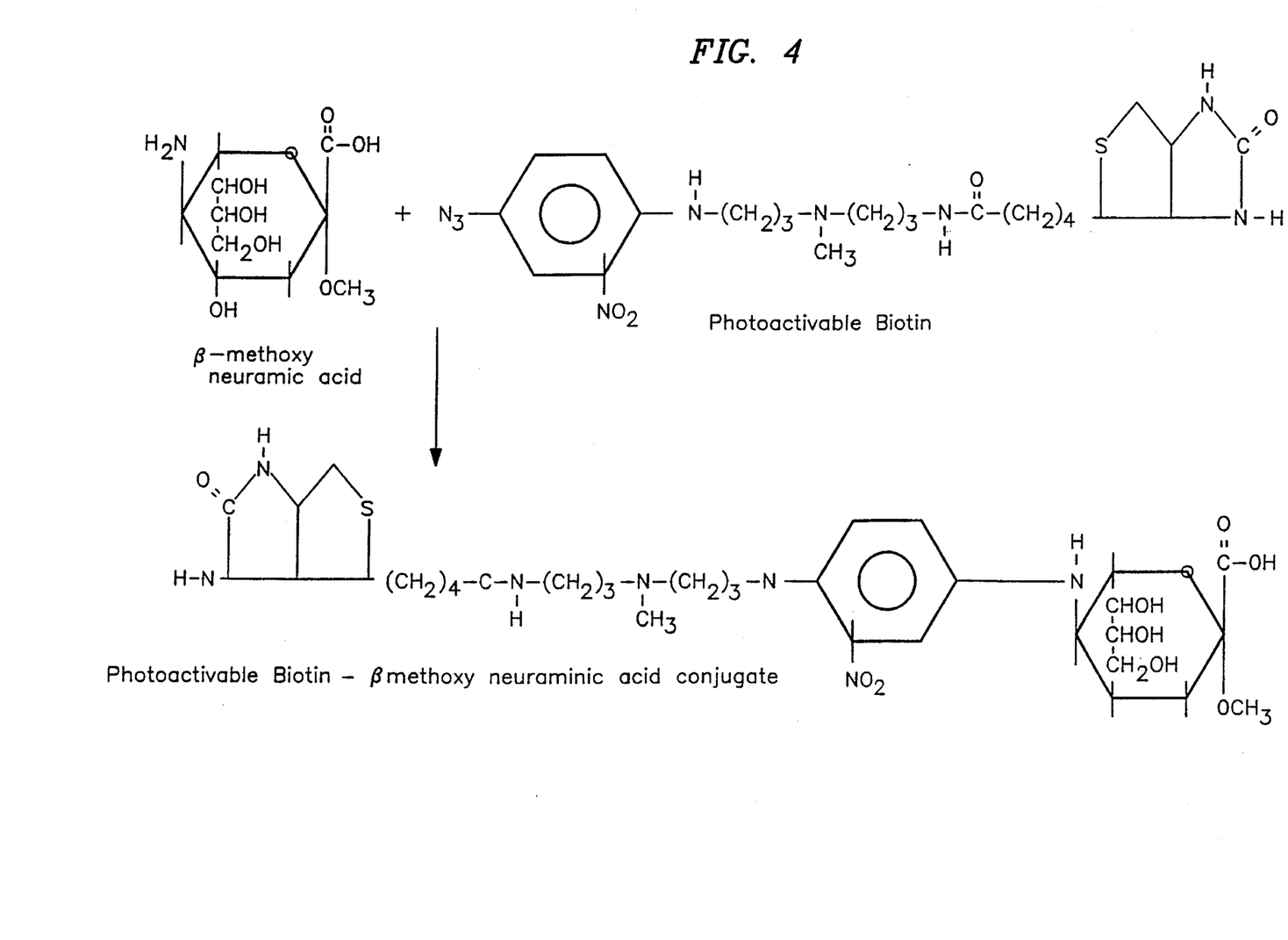
FIG. 4 illustrates another synthetic pathway by which a secondary amide linkage can be formed between B-methoxyneuraminic acid and photoactivatable biotin resulting in a biotin B-methoxyneuraminic acid conjugate. The conjugate can then be attached to biotin phosphatidyl ethanol amine, which is anchored in the vesicle membrane or in particulate matter, via a bridging molecule such as streptavidin.
Figure 5:
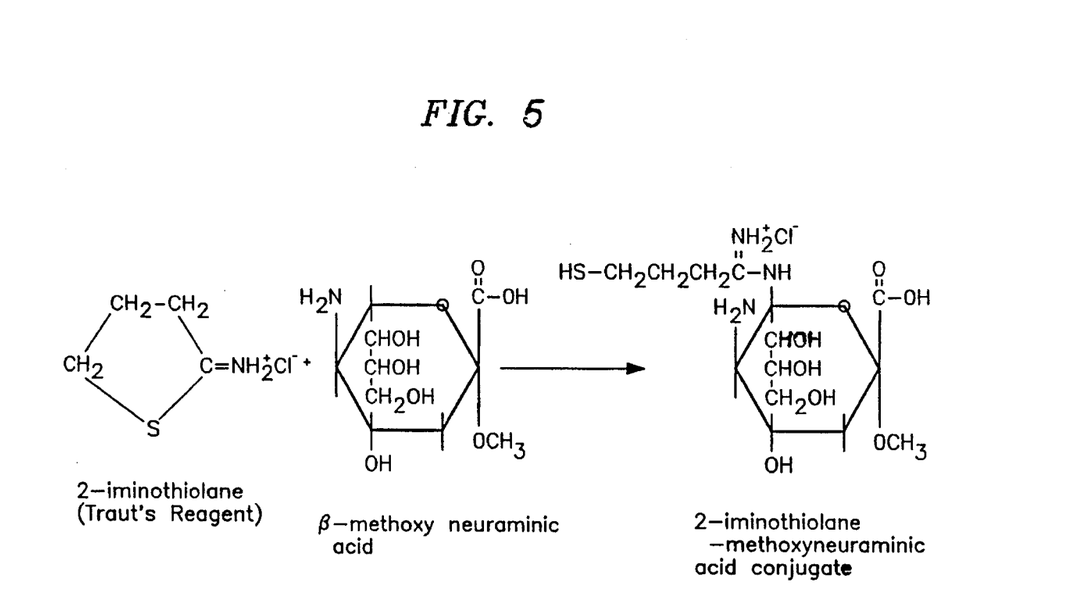
FIG. 5 shows the third type of synthetic pathway which would result in a bond formation between B-methoxyneuraminic acid and 2-iminothiolane (Traut's Reagent), resulting in yet another secondary amine bond that is not hydrolyzable by the circulating endogenous enzyme neuraminidase.
Figure 6A:
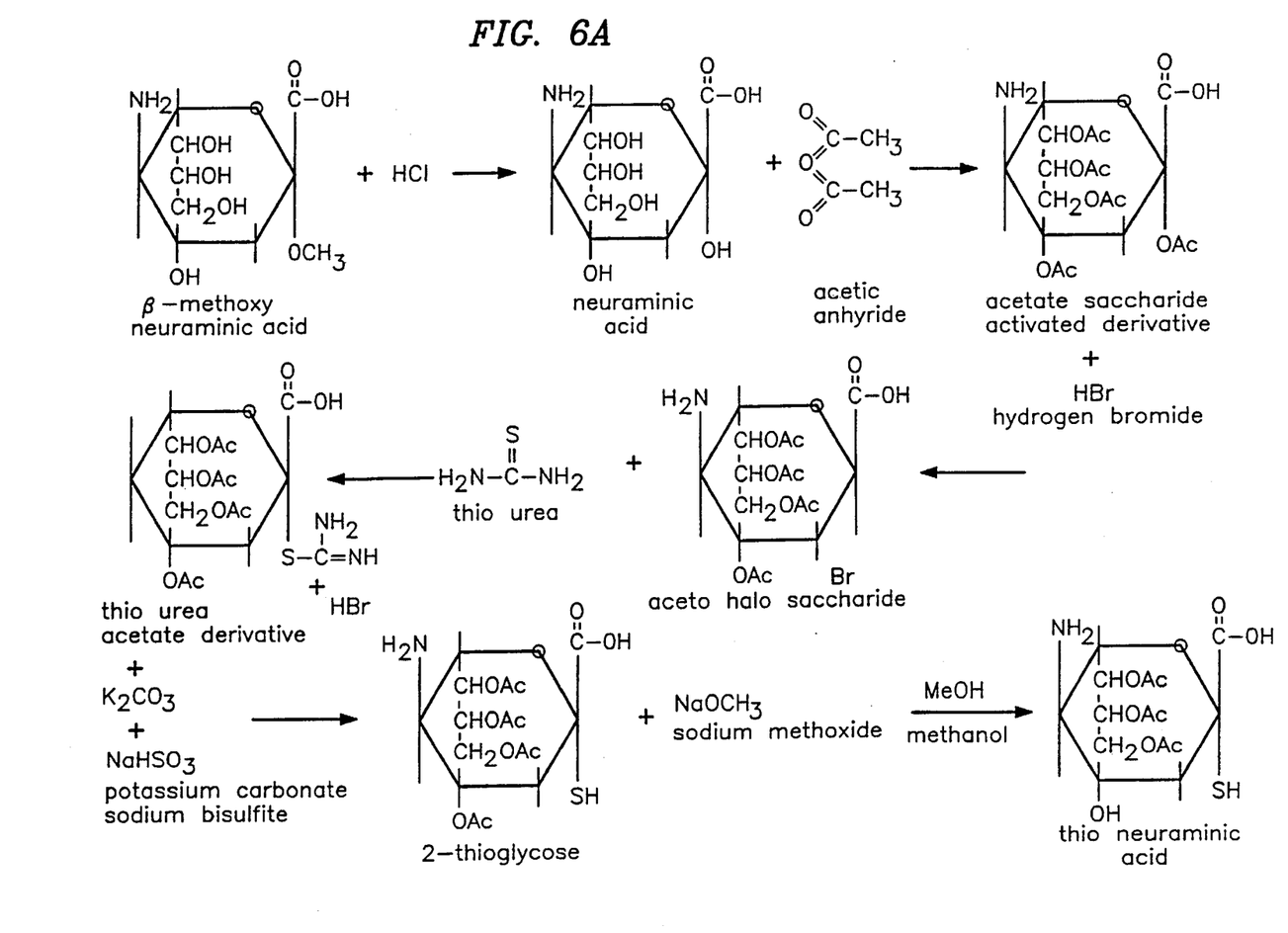
FIG. 6A and 6B show another synthetic pathway for establishing a non-hydrolyzable bond between neuraminic acid and p-maleimido phenyl butyrate phosphatidyl ethanol amine through the formation of a thio ether bond.
Figure 6B:
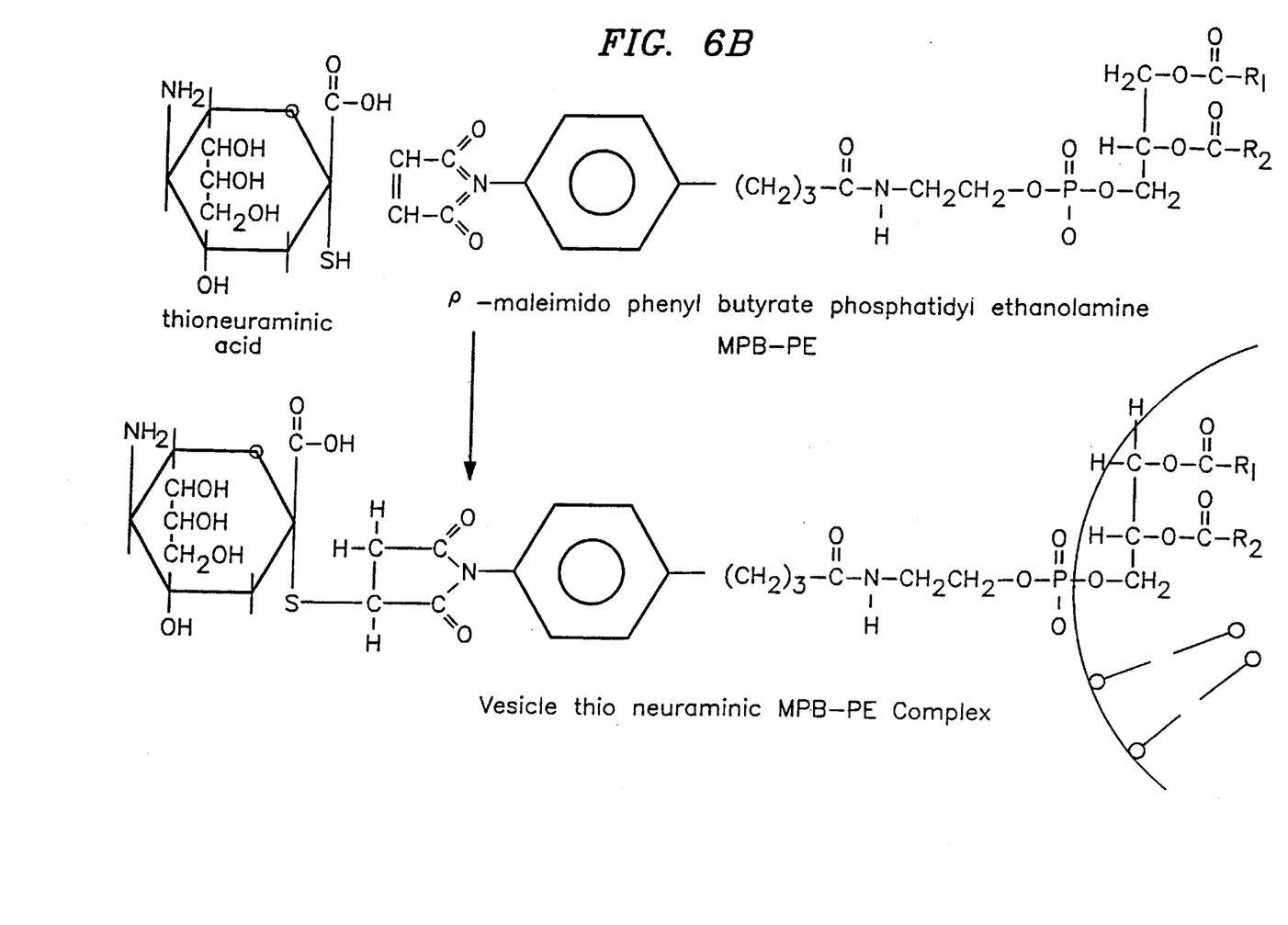

FIG. 3 illustrates the first example of a synthetic pathway by which a nonhydrolyzable amide bond is created to connect the B-methoxyneuraminic acid sugar to an appropriate bridging molecule.

Reference character "b" of FIG. 3 points out an

|     | DSL | DCP | CHOL | MPB-PE | DERIVATIZED NEURAMINIC ACID | GANGLIO-SIDE |
| --- | --- | --- | --- | --- | --- | --- |

1. DSL = Distearoyl Lecithin
2. DCP = Dicetyl phosphate
3. CHOL = Cholesterol
4. MPB-PB = p-maleimido phenyl butyrate phosphatidyl ethanol amine The liposomes were made using the method described in U.S. Pat. No. 4,603,044. Briefly, the crusts, having the above compositions, were solubilized with 10.0 ml of 10 mM phosphate buffer, pH 7.4, to which a 10 ul aliquot of $^{125}$I-human growth hormone was added. The mixture was sonicated on a Heat Systems Branson Cell Disrupter at setting #4 for 6.0 minutes at 60° C. The sample was then centrifuged for one hour at 20,000 rpm in a Sorvall RC2B centrifuge at 20° C. The supernatant was decanted and 410 ul was chromatographed over a sephadex G-100 column equilibrated with 10 mM phosphate buffer, pH 7.4. The derivatised neuraminic acid (DERIV. N.A.) was then added to the liposomes for the DERIV N.A. sample and allowed to react with the MPB-PE that was already in the liposomal membrane.

Figure 7:
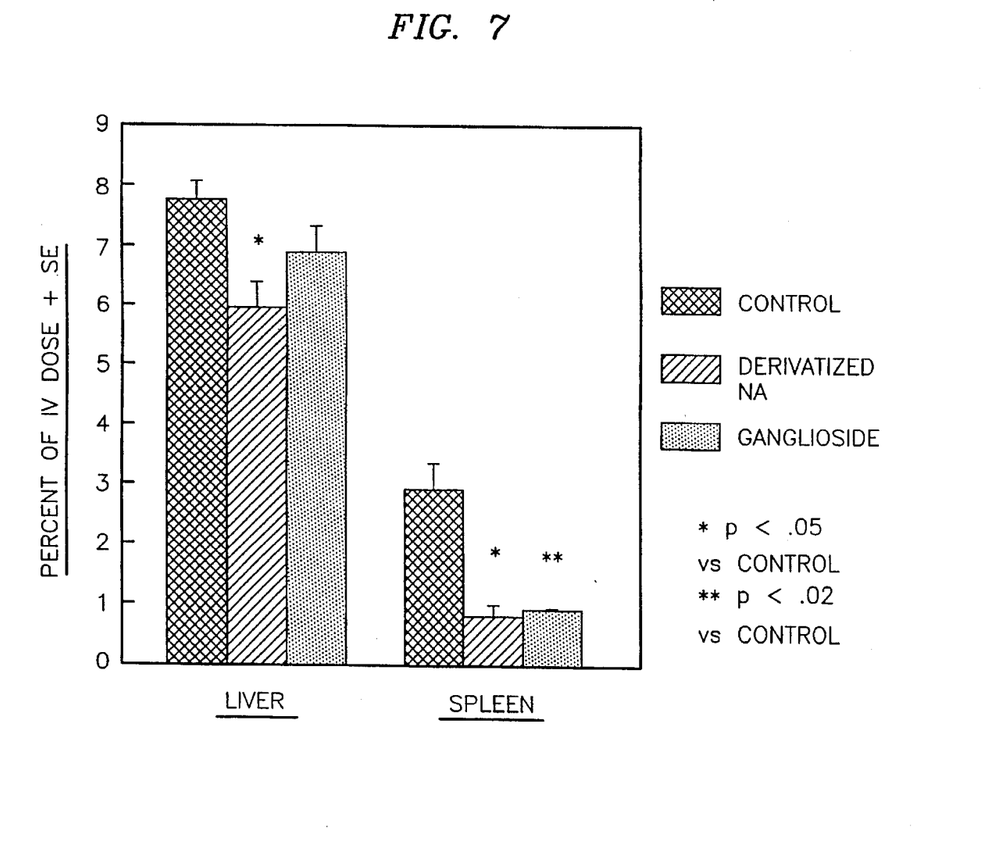
FIG. 7 is a graph showing the 2-hour effect of neuraminic acid on I.V. liposome distribution.

These test samples were then tested in normal rats. In the rat study, five rats were used for each group. The test samples were administered intravenously to each rat and the rats' livers and spleens were removed after two hours, under seconal anesthesia, and processed for counting the radio-label. The results of the study are shown in FIG. 7. The rats that received the liposomes with the synthetically-derived neuraminic acid had significantly fewer liposomes in their livers and spleens than rats receiving the control liposomes without any neuraminic acid. Synthetically-derived neuraminic acid is B-methoxyneuraminic acid that has been derivatized according to the above specification and does not contain a glycosidic bond that is hydrolyzable by circulating endogenous enzymes, such as neuraminidase.

The rats that received the liposomes with the naturally-occurring sialic acid ganglioside showed significantly lower levels of liposomes in their livers than the comparable control rats, but not as low a level of liposomes as was observed in rats receiving the liposomes with the synthetic neuraminic acid derivative. The naturally-occurring ganglioside is a molecule that exhibits a terminal sialic acid residue accompanied by a penultimate galactose group. The sialic acid residue of that ganglioside is connected to a penultimate sugar moiety by a glycosidic bond that is hydrolyzable by the enzyme neuraminidase. In the case of "GM-1" ganglioside the sialic acid residue is attached to an internal galactose. The spleens of the rats receiving both the synthetic neuraminic acid and the natural ganglioside were lower than the control rats.

EXAMPLE #2

Figure 8:
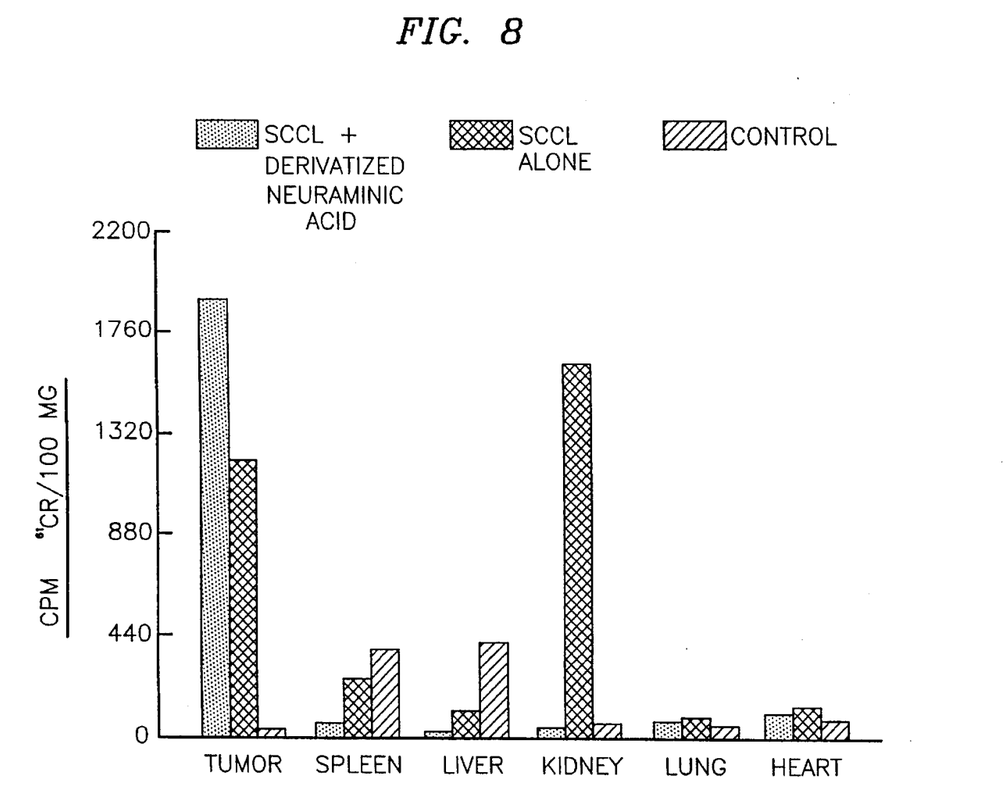
FIG. 8 is a graph showing the effect of neuraminic acid on in vivo delivery of liposomes with small cell carcinoma (SCCL) antibodies, marked by $^{51}$Chromium radiation.

Avoidance of Liver, Spleen and Heart in Nude Mice with Liposomes Targeted to Tumors Three types of liposomes were prepared Sample A: Tumor-specific antibody (SCCL-1); with synthetic neuraminic acid Sample B: Tumor-specific antibody (SCCL-1); no synthetic neuraminio acid Sample C: Control (non-specific) antibody; no synthetic neuraminic acid Nude mice with xenografted human Small Cell Carcinoma of the Lung (SCCL) were used. Each liposome sample A, B, and C, was subcutaneously injected into the mice. The mice were sacrificed at forty-eight hours and their various tissues were removed for analysis of the radio-label. The data are shown in FIG. 8. It is clearly shown that the most effective binding to the tumor occurred with the liposomes that were both attended to SCCL-1 antibody and were masked from liver and spleen uptake with the synthetic neuraminic acid. The liposomes with the SCCL-1 antibody still did significant targeting to the tumor, but some of the liposomes were found in other tissues. The liposomes that had neither site-binding antibodies of synthetic neuraminic acid were found in significant amounts in liver, spleen, and lung.

A generic representation of naturally-occurring neuraminic acid is shown in FIG. 1.

Five derivatives found naturally in man are:

1. Ned 5 Ac
2. Ned 5,9 Ac$^2$
3. Ned 5,7,9 Ac$^3$
4. Ned 5 Ac 9 Lt
5. Ned 5 Gc

Definitions:

Neu=Neuraminic acid

Ac=acetyl—CH$_3$CO—

Gc=glycolyl=OHCH$_2$CO

Lt=lactyl=CH$_3$(CHOH)CO

Neuraminic acid and its above-described derivatives are found naturally in warm-blooded hosts and are known generally as sialic acid and sialic acid derivatives. GM-1 is a natural sialic acid derivative commonly used for masking liposomes from the RES. The use of sialic acid and its naturally-occurring derivatives for extending the in vivo circulating and binding life of liposomes or particulate matter is limited however, because endogenous enzymes circulating in the plasma, such as neuraminidase, cleave the sialic acid or its derivative from the liposome or particulate matter. The unmasked liposomes or particulate matter are then exposed to the RES, and phagocytosed.

It was discovered by the applicants herein, that this cleavage problem can be solved by using a synthetic sialic acid that forms a non-hydrolyzable bond with the liposome or particulate matter. While not the preferred embodiment of this invention, the derivatives of natural sialic acid shown above may also be synthetically attached via a non-hydrolyzable bond by removing the N-acetyl group in examples #1–4 or the N-glycol group in example #5. The net effect of this removal is to expose a primary amino group which can be derivatized with succinimidyl acetyl thio acetic acid to form an amide linkage (—CONH—) which is a bond that cannot be hydrolyzed by a circulating endogenous enzyme such as neuraminidase. This new series of synthetically-manipulated neuraminic acid derivatives, when attached to liposomes or particulate matter, provide superior masking from the RES.

Figure 2:
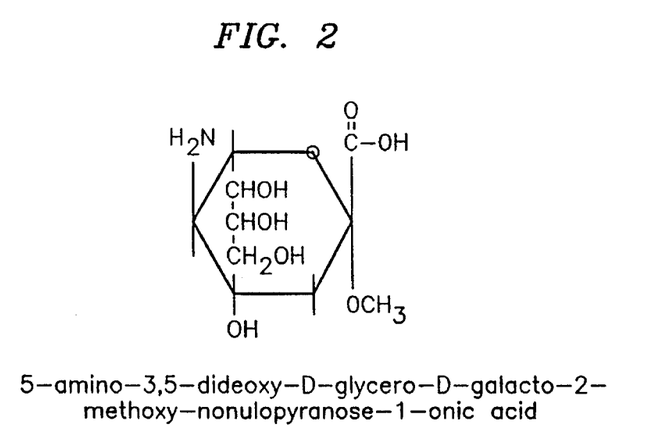
FIG. 2 represents B-methoxyneuraminic acid structure.

The preferred embodiment, however, is the synthetic, B-methoxy form of neuraminic acid shown in FIG. 2.

EXAMPLE #3

Anti-HIV Protease Inhibitor Delivered by CD4 Site-Binding Liposomes Masked with Synthetic Neuraminic Acid Anti-HIV protease inhibitor was made the active agent cargo of a liposome. CD4 molecules were covalently linked to the surface of the liposome, to act as site-specific molecules which would bind the liposome to an HIV-infected cell. Synthetic neuraminic acid molecules were covalently linked to the liposome to mask the liposome from the reticuloendothelial system.

In vitro studies using administered doses of this site-specific liposomal protease inhibitor agent demonstrated nearly ten-fold greater anti-viral activity over protease inhibitors not so administered. Similar beneficial results would be expected in vivo for inhibitors delivered by liposomes or particulate matter with covalently linked CD4 and synthetic neuraminic acid masking molecules.

Example #4

Enhanced Delivery of Anti-Infective Agents by Liposomes or Other Delivery Mediums Targeted to Delivery Sites By Monoclonal Antibodies and Masked From the Reticuloendothelial System (RES) By Synthetic Neuraminic Acid An increasing number of infective agents such as viruses and bacteria are becoming resistant to drug therapy. For example, treatment of AIDS patients with the bacterial infection *M. Avium intracelluleare* is hampered by antibiotic resistance. Clinically, this resistance presents a serious problem in terms of effective treatment of the individual patient as well as the general population to which these untreatable infections may spread.

This infection presents a means by which such resistant infectious agents may be treated. To illustrate, applicants successfully delivered an antibiotic drug to the surface of an *M. Avium intracelluleare* microorganism by targeting the drug's liposome carrier with an *M. Avium intracelluleare*-specific monoclonal antibody. The liposome circulated to its intended site of action, avoiding the body's reticuloendotheiial system, by having attached a masking component, synthetic neuraminic acid. Upon binding to the bacterium, the liposome released its antibiotic cargo, thereby overcoming the organism's resistance by delivering a high concentration of the drug to a localized site.

Data from in vitro studies indicate that in vivo administered doses of site-specific liposomal-couried or particulate matter-couried anti-microbial agents should demonstrate significantly greater anti-microbial activity over like agents not so administered.

What is claimed is:

1. A composition of matter for internal administration in the therapeutic or diagnostic treatment of a warm-blooded animal comprising:

a first component which comprises liposomes;

a second component which is a synthetic neuraminic acid molecule attached to the liposome wall, said synthetic neuraminic acid selected from the group consisting of neuraminic acid with a methoxy group on carbon 2, neuraminic acid with an N-acetyl group attached to the nitrogen on carbon 5, neuraminic acid with N-acetyl groups attached to the nitrogen on carbon 5 and to the oxygen on carbon 9, neuraminic acid with an N-acetyl group attached to the nitrogen on carbon 5 and a lactyl group attached to the oxygen on carbon 9, or neuraminic acid with an N-acetyl group attached to the nitrogen on carbon 5 and an N-glycolyl group attached to the oxygen on carbon 9, that prevent phagocytosis of the liposome by the body's reticuloendothelial system and which cannot be cleaved by the body's endogenous enzymes; and, a third component, which is a target-specific molecule attached to the liposome wall to deliver liposomes to specific sites in the body.

2. A composition of matter as defined in claim 1, wherein the neuraminic acid has a methoxy group on carbon 2.

3. A composition of matter as defined in claim 1, wherein the neuraminic acid has an N-acetyl group attached to the nitrogen on carbon 5.

4. A composition of matter as defined in claim 1, wherein the neuraminic acid has acetyl groups attached to the nitrogen on carbon 5, and to the oxygen on carbon 9.

5. A composition of matter defined in claim 1, wherein the neuraminic acid has acetyl groups attached to the nitrogen on carbon 5, to the oxygen on carbon 7, and to the oxygen on carbon 9.

6. A composition of matter defined in claim 1, wherein the neuraminic acid has an N acetyl group attached to the nitrogen on carbon 5, and a lactyl group attached to the oxygen on carbon 9.

7. A composition of matter defined in claim 1, wherein the neuraminic acid has an N glycolyl group attached to the nitrogen on carbon 5.

* * * * *